(12) United States Patent
Minnette

(10) Patent No.: US 9,682,805 B2
(45) Date of Patent: Jun. 20, 2017

(54) CLOSURE FOR CONTAINER

(71) Applicant: Berry Plastics Corporation, Evansville, IN (US)

(72) Inventor: Jeffrey C Minnette, Evansville, IN (US)

(73) Assignee: Berry Plastics Corporation, Evansville, IN (US)

( * ) Notice: Subject to any disclaimer, the term of this patent is extended or adjusted under 35 U.S.C. 154(b) by 0 days.

(21) Appl. No.: 14/063,681

(22) Filed: Oct. 25, 2013

(65) Prior Publication Data

US 2014/0116977 A1    May 1, 2014

Related U.S. Application Data

(60) Provisional application No. 61/719,232, filed on Oct. 26, 2012, provisional application No. 61/826,568, filed on May 23, 2013.

(51) Int. Cl.
| | |
|---|---|
| *B65D 79/00* | (2006.01) |
| *B65D 51/14* | (2006.01) |
| *B65D 41/04* | (2006.01) |
| *B65D 53/02* | (2006.01) |
| *B65D 55/02* | (2006.01) |
| *A61L 2/04* | (2006.01) |

(52) U.S. Cl.
CPC .......... *B65D 55/026* (2013.01); *B65D 41/04* (2013.01); *B65D 41/045* (2013.01); *B65D 41/0442* (2013.01); *B65D 41/0457* (2013.01); *B65D 41/0492* (2013.01); *B65D 51/145* (2013.01); *B65D 53/02* (2013.01); *B65D 79/005* (2013.01); *A61L 2/04* (2013.01)

(58) Field of Classification Search
CPC ... B65D 51/145; B65D 79/005; B65D 41/045
USPC ........ 215/230, 347, 349, 350, 351, 270, 274
See application file for complete search history.

(56) References Cited

U.S. PATENT DOCUMENTS

| | | |
|---|---|---|
| 87,274 A | 2/1869 | Mason |
| 1,172,483 A | 2/1916 | Rike et al. |
| 2,816,697 A | 12/1957 | Amberg |
| 3,178,051 A | 4/1965 | Bryant |
| 3,237,803 A | 3/1966 | Bryant |
| 3,325,048 A | 6/1967 | Edwards |
| 3,375,954 A | 4/1968 | Arvid et al. |
| 3,420,397 A | 1/1969 | Miller |

(Continued)

FOREIGN PATENT DOCUMENTS

| | | |
|---|---|---|
| WO | 2010/045699 A1 | 4/2010 |
| WO | 2012/075556 A1 | 6/2012 |

OTHER PUBLICATIONS

PCT International Search Report and Written Opinion completed by the ISA/EP on Mar. 3, 2014 and issued in connection with PCT/US2013/066899.

(Continued)

*Primary Examiner* — Jeffrey Allen
*Assistant Examiner* — Jennifer Castriotta
(74) *Attorney, Agent, or Firm* — Barnes & Thornburg LLP

(57) ABSTRACT

A canister includes a container and a closure. The container is formed to include a product-storage region and an open mouth that opens into the product-storage region. The closure is configured to couple to the container to close the open mouth.

30 Claims, 9 Drawing Sheets

(56) References Cited

U.S. PATENT DOCUMENTS

| | | | |
|---|---|---|---|
| 3,425,382 A | 2/1969 | Johnson | |
| 3,468,467 A | 9/1969 | Amberg | |
| 3,471,075 A | 10/1969 | Wolf | |
| 3,485,412 A | 12/1969 | Hawley | |
| 3,580,468 A | 5/1971 | McDevitt | |
| 3,648,888 A | 3/1972 | Cheladze | |
| 3,930,589 A * | 1/1976 | Koontz | 215/352 |
| 3,995,740 A | 12/1976 | Amberg | |
| 4,049,122 A | 9/1977 | Maxwell | |
| 4,093,094 A * | 6/1978 | Smalley | B65D 51/145 |
| | | | 215/276 |
| 4,102,454 A | 7/1978 | Karevaara | |
| 4,106,397 A | 8/1978 | Amberg | |
| 4,117,971 A | 10/1978 | Itoh | |
| 4,122,964 A | 10/1978 | Morris | |
| 4,349,400 A | 9/1982 | Gilden | |
| 4,448,345 A * | 5/1984 | Helms | 229/123.1 |
| 4,616,761 A * | 10/1986 | Nolan | 215/271 |
| 4,782,968 A | 11/1988 | Hayes | |
| 4,904,512 A | 2/1990 | Yamada | |
| 5,040,691 A | 8/1991 | Hayes et al. | |
| 5,062,568 A | 11/1991 | Hill | |
| 5,094,603 A | 3/1992 | Gellert | |
| 5,240,131 A | 8/1993 | Keller | |
| 5,725,120 A | 3/1998 | Ramsey et al. | |
| 5,820,016 A | 10/1998 | Stropkay | |
| 5,839,592 A * | 11/1998 | Hayes | B32B 27/08 |
| | | | 215/230 |
| 6,095,359 A | 8/2000 | Richmond | |
| 6,220,466 B1 | 4/2001 | Hayes et al. | |
| 6,364,201 B1 | 4/2002 | Varano | |
| 6,413,625 B2 | 7/2002 | Rolle | |
| 6,588,654 B2 | 7/2003 | Nakashima | |
| 7,100,770 B2 | 9/2006 | DAmato | |
| 7,281,649 B2 | 10/2007 | Pyper, Jr. | |
| 7,481,356 B2 | 1/2009 | Stahlecker | |
| 7,611,026 B1 | 11/2009 | Bloom et al. | |
| 7,677,435 B2 | 3/2010 | Stahlecker | |
| 7,905,821 B2 | 3/2011 | Stahlecker | |
| 7,972,669 B2 | 7/2011 | Matsuoka | |
| 7,984,846 B2 | 7/2011 | Messerschmid | |
| 8,146,796 B2 | 4/2012 | DAmato | |
| 8,172,127 B2 | 5/2012 | Frost | |
| 8,323,164 B2 | 12/2012 | Messerschmid | |
| 2003/0098286 A1 | 5/2003 | Bloom et al. | |
| 2005/0284837 A1 | 12/2005 | Taber et al. | |
| 2006/0118608 A1 | 6/2006 | Stahlecker | |
| 2007/0187352 A1 | 8/2007 | Kras et al. | |
| 2009/0159653 A1 | 6/2009 | Stahlecker | |
| 2009/0184020 A1 | 7/2009 | Messerschmid | |
| 2010/0184877 A1 | 7/2010 | Miyagawa | |
| 2011/0174656 A1 | 7/2011 | DAmato | |
| 2011/0281704 A1 | 11/2011 | Messerschmid | |
| 2012/0241511 A1 | 9/2012 | Marshall | |
| 2012/0318805 A1 | 12/2012 | Leser | |
| 2013/0001287 A1 | 1/2013 | Stahlecker | |

OTHER PUBLICATIONS

International Search Report and Written Opinion for International Application No. PCT/US2014/028882, Aug. 5, 2014, 10 pages.
Canning Lids 101, available from https://www.freshpreserving.com/canning-lids-101.html, retrieved on Jan. 31, 2017, 2 pages.

* cited by examiner

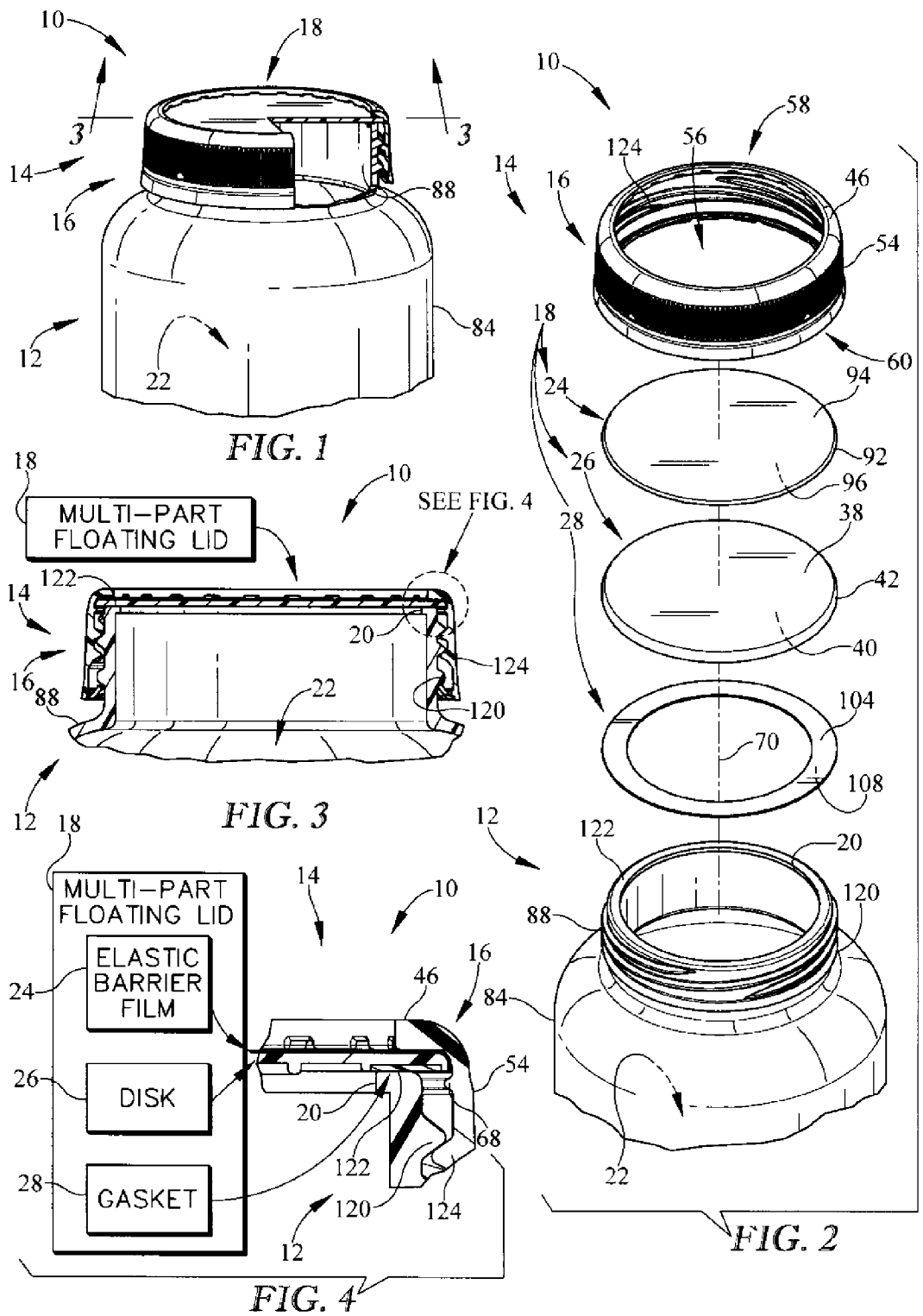

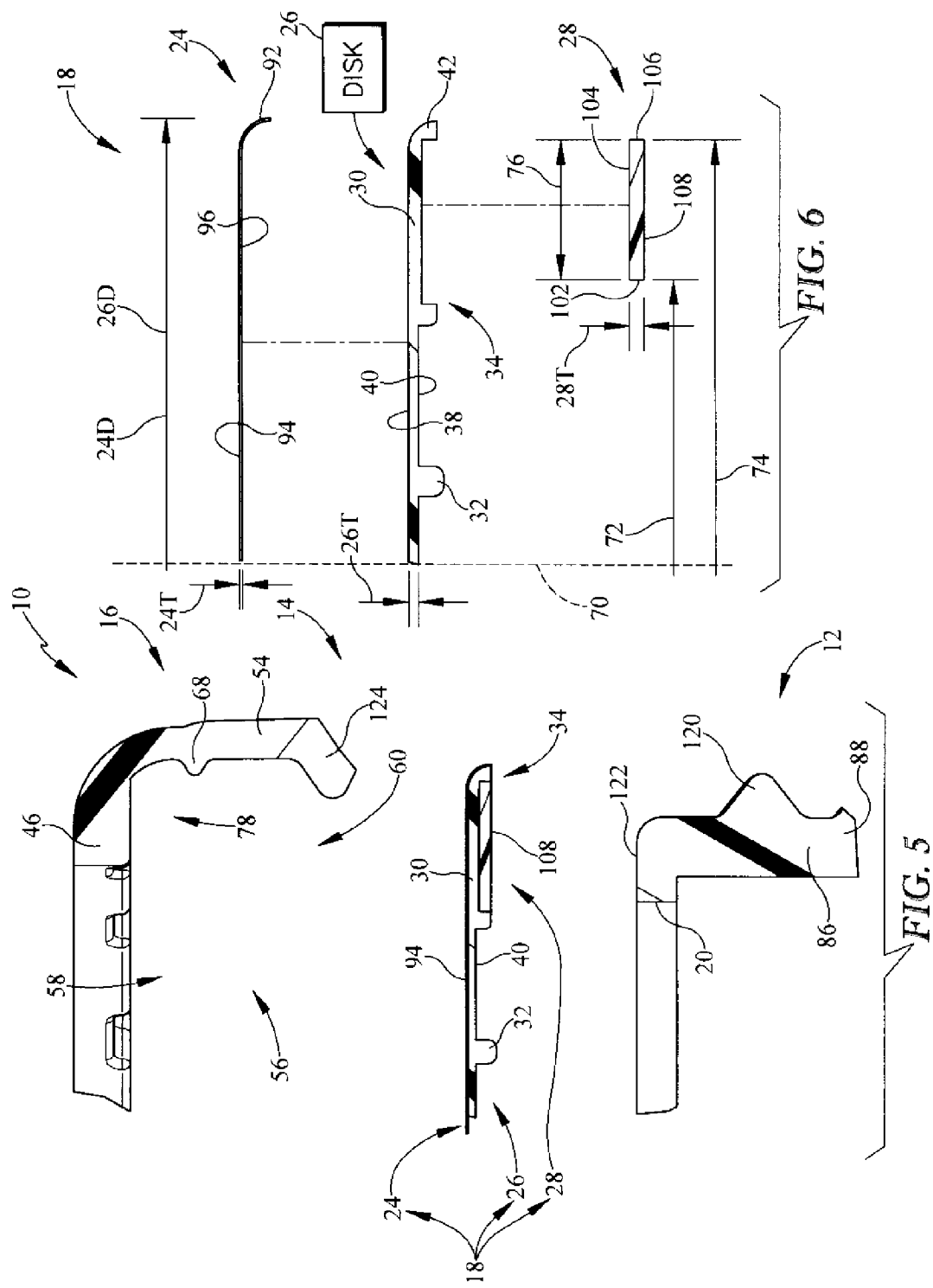

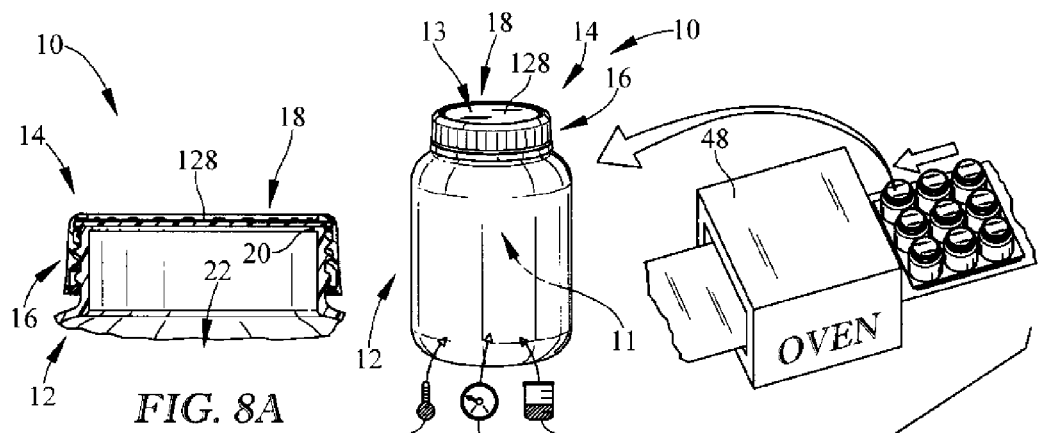
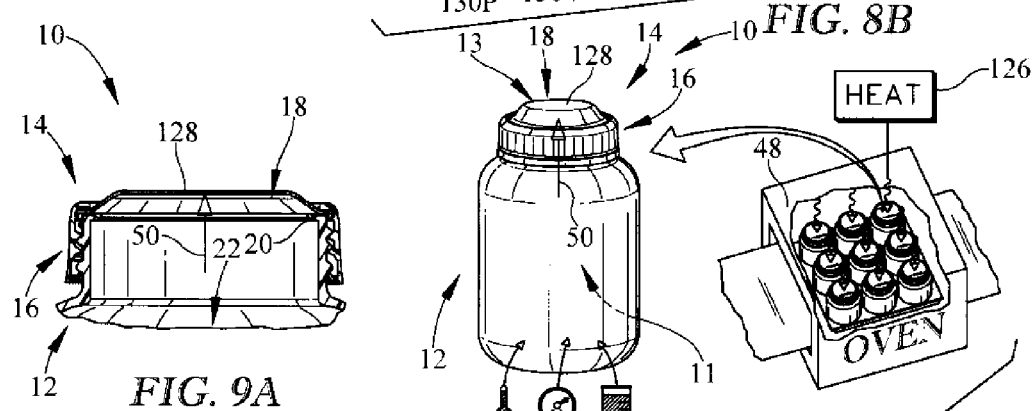
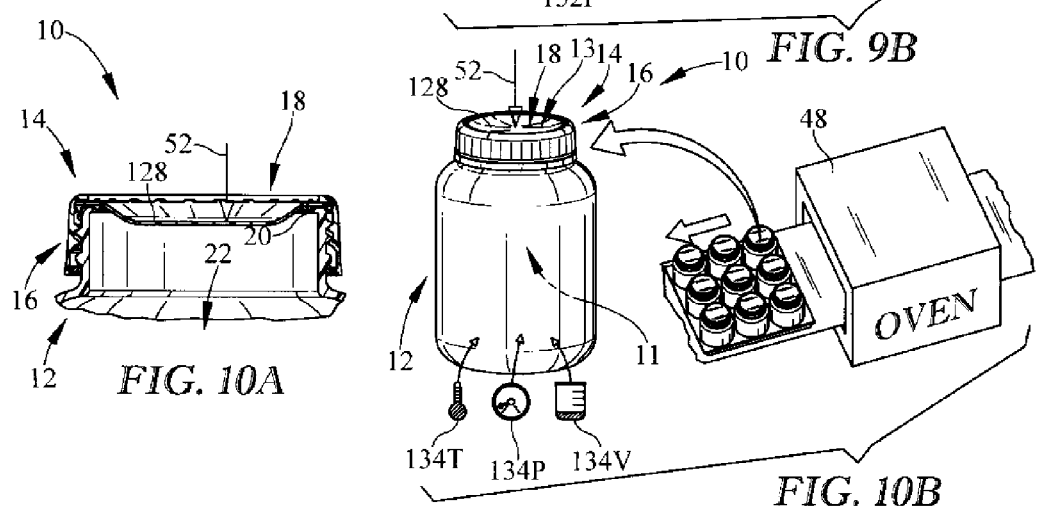

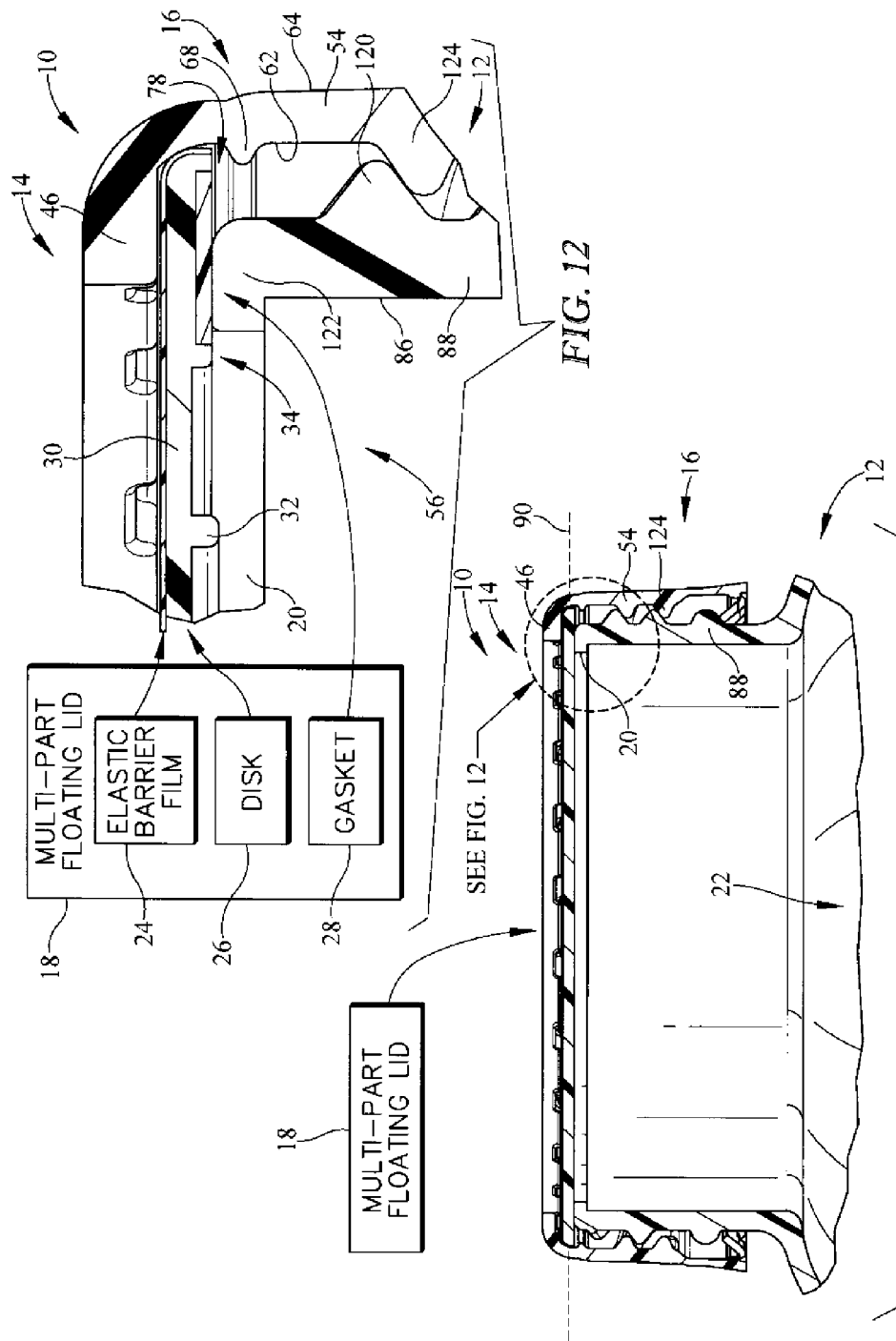

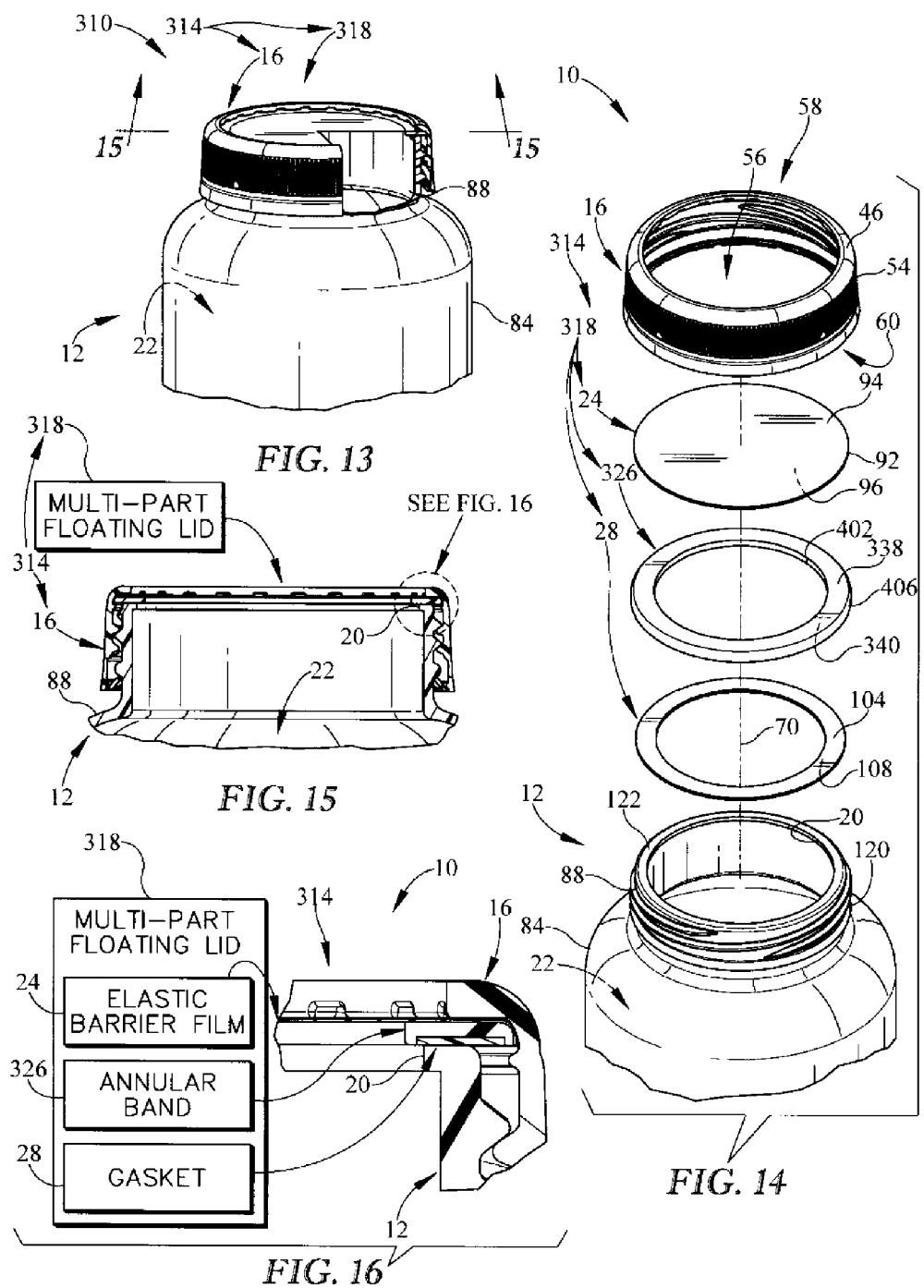

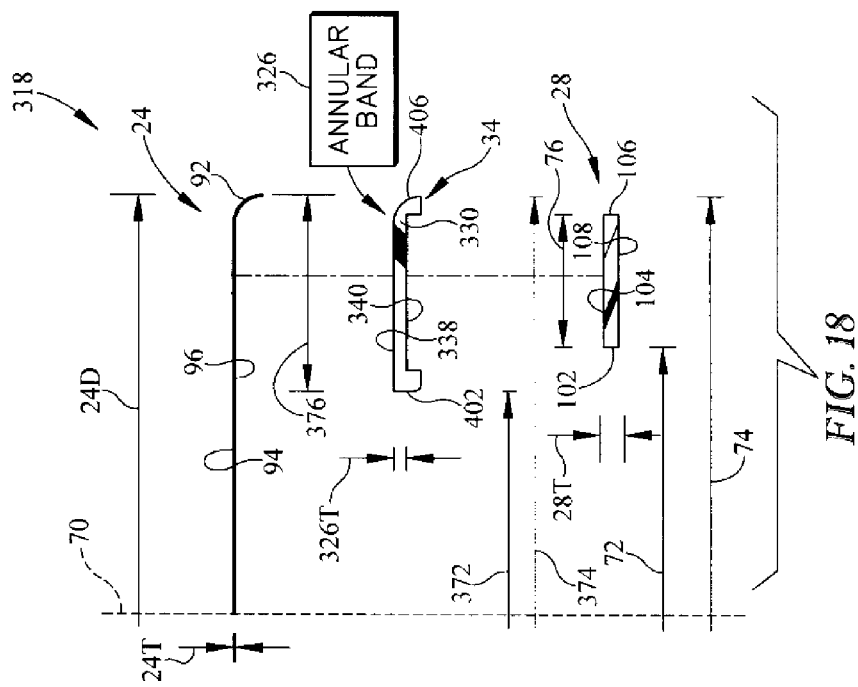
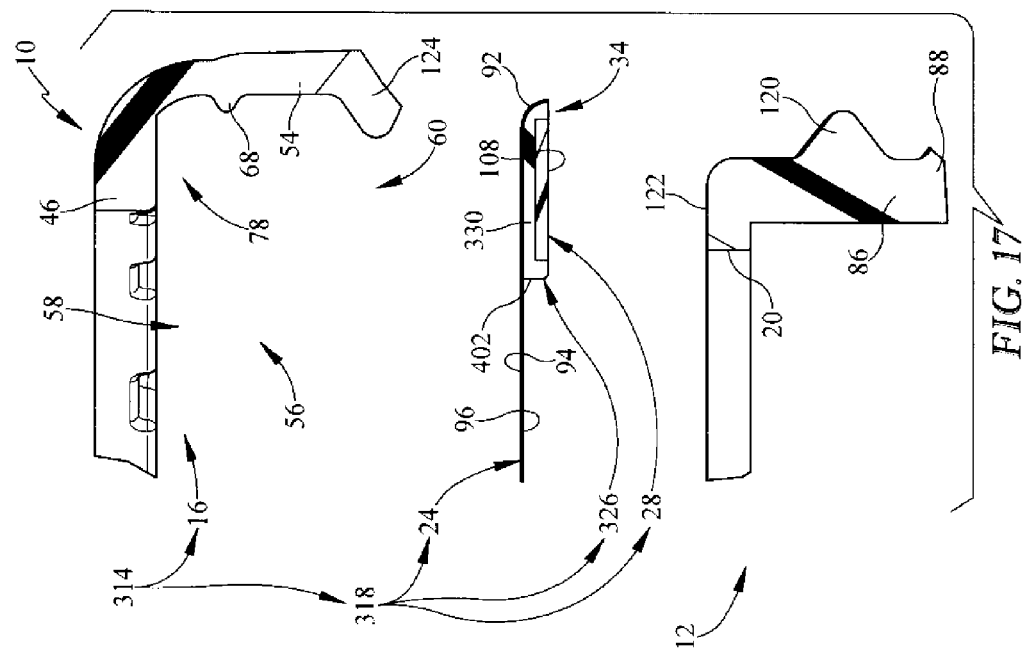

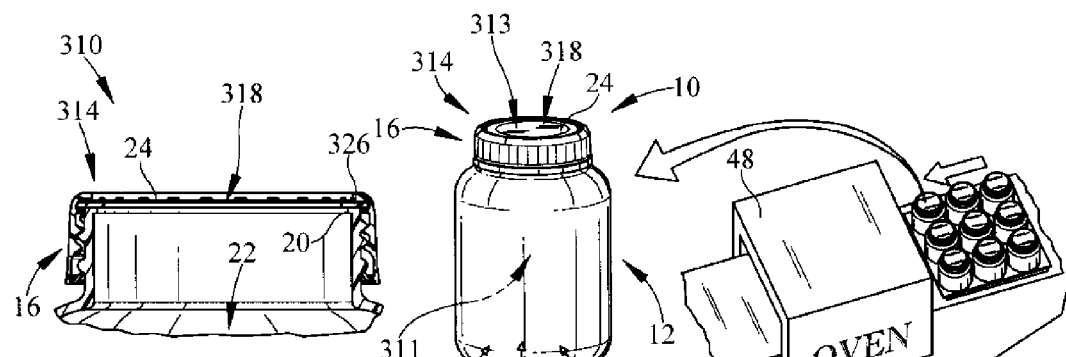
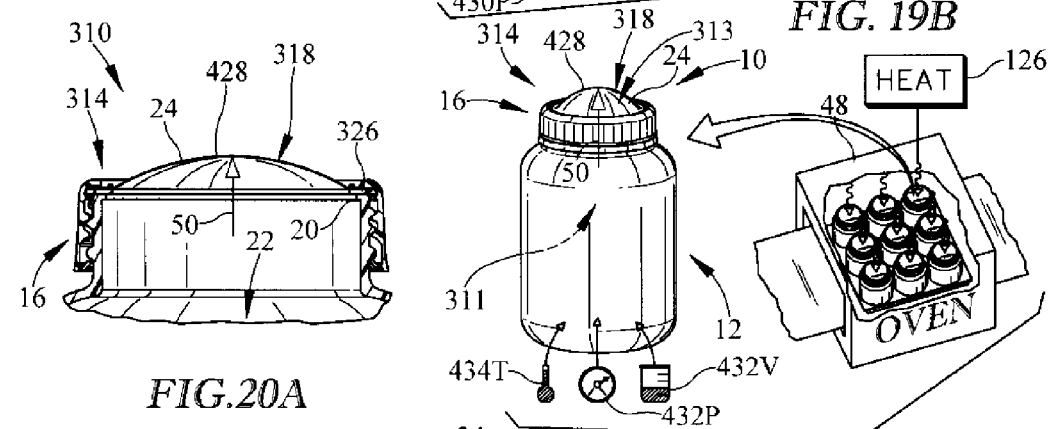
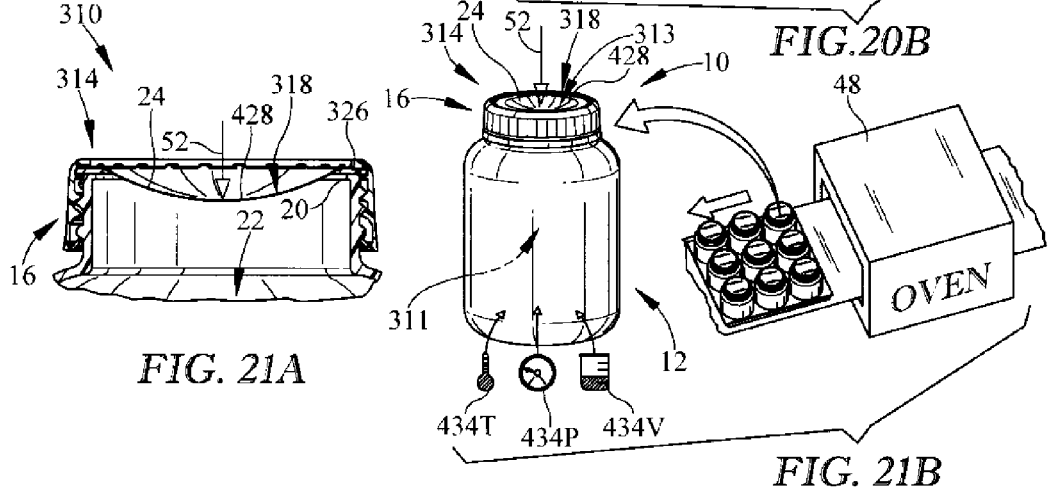
FIG. 19A
FIG. 19B
FIG. 20A
FIG. 20B
FIG. 21A
FIG. 21B

CLOSURE FOR CONTAINER

PRIORITY CLAIM

This application claims priority under 35 U.S.C. §119(e) to U.S. Provisional Application Ser. No. 61/719,232, filed Oct. 26, 2012, and Ser. No. 61/826,568, filed May 23, 2013, which are expressly incorporated by reference herein.

BACKGROUND

The present disclosure relates to closures for mounting on top of bottles or other containers, and in particular, to a closure including a lid and a ring. More particularly, the present disclosure relates to a closure that can withstand a high pressure and high temperature sterilization process known as retort.

SUMMARY

A canister in accordance with the present disclosure includes a container and a closure. The container is formed to include a product-storage region and an open mouth that opens into the product-storage region. The closure is configured to couple to the container to close the open mouth.

In illustrative embodiments, the closure includes a lid-retainer ring for mating with a filler neck of the container and a multi-part floating lid configured to be trapped between the filler neck and the lid-retainer ring to close the open mouth. The closure, when coupled to the container, is configured to withstand a high pressure and high temperature sterilization process known as retort. The multi-part floating lid is located and trapped between the lid-retainer ring and a brim included in the container when the closure is coupled to the container.

In illustrative embodiments, the multi-part floating lid includes a lid-reinforcing core, an elastic barrier film coupled to an upwardly facing outer surface of the lid-reinforcing core, and a gasket coupled to downwardly facing inner surface of the lid-reinforcing core. In illustrative embodiments, the lid-reinforcing core is a disk. During retort, high pressure is formed in the product-storage region of the container that may cause portions of the elastic barrier film and disk to expand and move through an aperture formed in the lid-retainer ring. After retort, low pressure is formed in the product-storage region of that container that may cause portions of the elastic barrier film and disk to contract and move through the open mouth formed in the container.

In illustrative embodiments, the disk is configured to provide means for supporting the elastic barrier film during deformation of the closure before, during, and after retort. The disk also minimizes a risk of damage to the closure and minimizes formation of an opening in the closure in response to an unintended cut or poke to the elastic barrier film so that the open mouth formed in the container remains closed when the multi-part floating lid is coupled to the container by the lid-retainer ring.

In other illustrative embodiments, the lid-reinforcing core is an annular band. The elastic barrier film is coupled to an upwardly facing outer surface of the annular band and the gasket is coupled to downwardly facing inner surface of the annular band. In illustrative embodiments, the annular band is configured to provide means for supporting the elastic barrier film and the gasket during deformation of the closure before, during, and after retort. During retort, high pressure is formed in the product-storage region of the container that may cause portions of the elastic barrier film to expand and move through an aperture formed in the lid-retainer ring. After retort, low pressure is formed in the product-storage region of that container that may cause portions of the elastic barrier film to contract and move through the open mouth formed in the container.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which:

FIG. 1 is a partial perspective view of a canister in accordance with the present disclosure showing that the canister includes a container and a closure coupled to the container and that portions of the canister have been broken away to reveal that the closure includes an outer lid-retainer ring configured to mate with the container and an inner multi-part floating lid trapped between the lid-retainer ring and the container to close an open mouth formed in the container;

FIG. 2 is an exploded perspective assembly view of the canister of FIG. 1 showing that the container includes a filler neck coupled to an underlying body and formed to include an open mouth and showing that the closure includes, from top to bottom, a lid-retainer ring configured to be tightened onto a container filler neck to trap a multi-part floating lid between the lid-retainer ring and the container, a multi-part floating lid for closing an open mouth of the filler neck and showing that the multi-part floating lid includes an elastic barrier film, a lid-reinforcing core, and a gasket and showing that the lid-reinforcing core is a disk;

FIG. 3 is a sectional view taken along line 3-3 of FIG. 1 showing the closure tightened on the filler neck of the container to restrict movement of the multi-part floating lid and to close the open mouth included in the filler neck so that food products stored in the container are blocked from escaping the container through the open mouth;

FIG. 4 is an enlarged view of the circled region of FIG. 3 showing that the lid-retainer ring is formed to include a lid-retainer cavity and that the lid-retainer ring includes a top wall, a side wall extending downwardly to mate with the container, and a lid-retainer support that retains the multi-part floating lid in the lid-retainer cavity and showing that the gasket included in the multi-part floating lid engages a brim included in the filler neck of the container to block egress food products and ingress of contaminants from between the container and the closure;

FIG. 5 is an exploded assembly view of the enlarged partial view of the canister of FIG. 4 showing the assembled multi-part floating lid in spaced-apart relation between the lid-retainer ring and the filler neck of the container and suggesting that the gasket engages the brim of the container;

FIG. 6 is an exploded assembly view of the multi-part floating lid of FIG. 5 showing that the multi-part floating lid includes, from top to bottom, an elastic barrier film formed to mate with an upper surface of an underlying disk, a disk, and a gasket and showing that the disk is monolithic and includes a laterally extending disk body including the upper surface and an opposite lower surface, a downwardly extending annular disk-support ring coupled to the lower surface of the disk body, and a downwardly extending gasket-receiving track appended to the inner surface of the disk body at a perimeter portion of the disk and sized to receive the gasket therein as suggested in FIG. 5;

FIG. 7 is a diagrammatic view of the canister of FIG. 1 showing that the canister comprises the closure comprising the lid-retainer ring and the multi-part floating lid including the elastic barrier film including a polypropylene layer, a tie layer, a nylon layer, an Ethylene Vinyl Alcohol (EVOH) layer, a nylon layer, an EVOH layer, a nylon layer, a tie layer, and a polypropylene layer, the disk, and the gasket and the container;

FIGS. 8A-10B are a series of views showing the canister of FIGS. 1-3 undergoing a high-temperature sterilization process known as retort;

FIG. 8A is a sectional view similar to FIG. 3 of a canister on a conveyer moving toward an oven to undergo retort as suggested in FIG. 8B and showing that the canister has not entered the oven and, as such, the multi-part floating lid is un-deformed;

FIG. 8B is a diagrammatic view of a tray carrying nine canisters in accordance with the present disclosure and moving along the conveyor toward the oven to undergo retort and an enlarged perspective view of one of those canisters before it is heated and pressurized in the oven;

Figure 7:
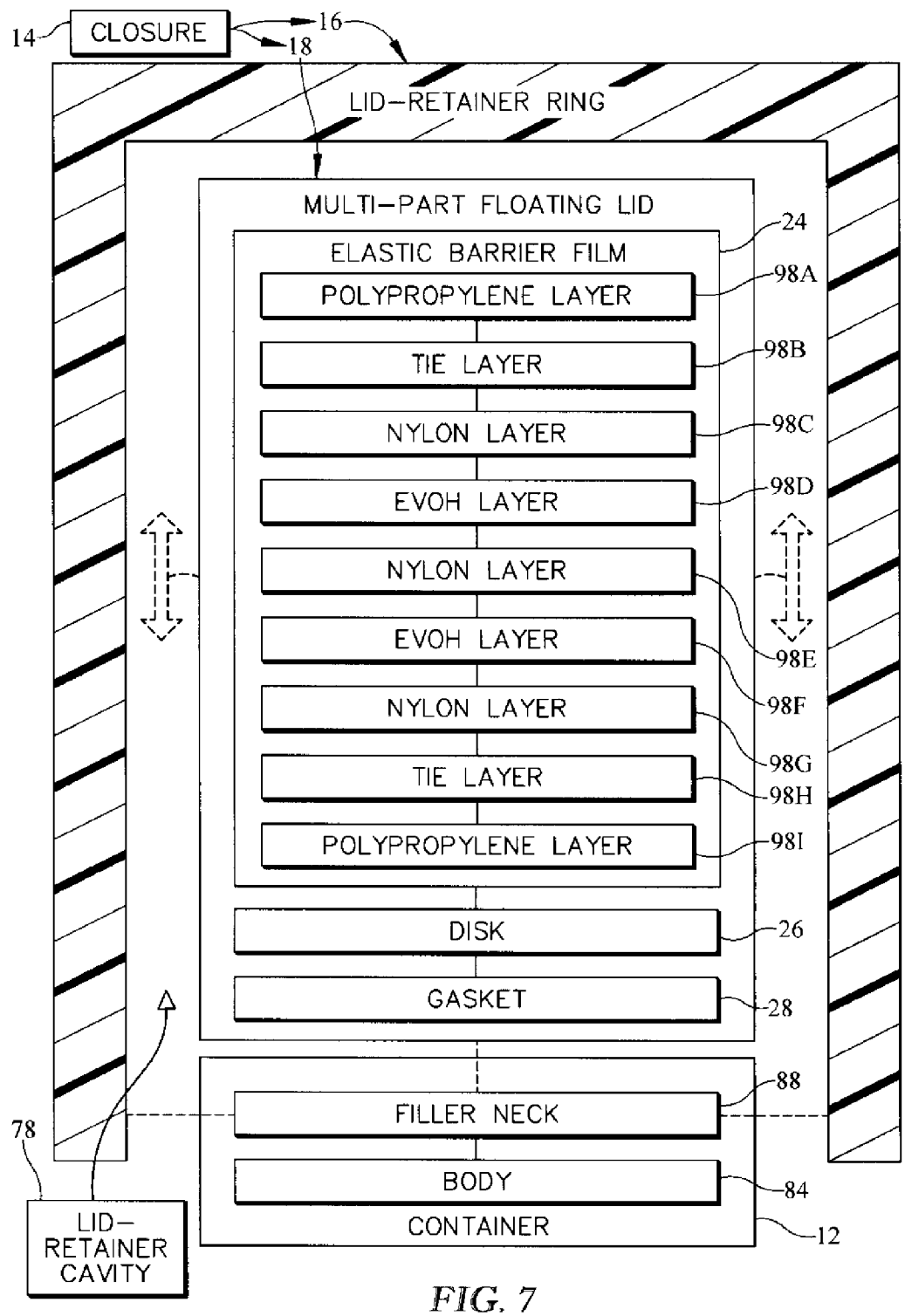
FIG. 7A is a view similar to FIG. 7 of another embodiment of an elastic barrier film in accordance with the present disclosure showing that the elastic barrier film includes a polypropylene layer, a tie layer, a nylon layer, a barrier layer, a nylon layer, a tie layer, and a polypropylene layer.

FIG. 9A is a view similar to FIG. 8A of the canister after it has been moved into the oven as suggested in FIG. 9B and showing that the canister is heated and pressurized within the oven to sterilize the canister and food products stored within the canister and that the heat and pressure inside the canister have caused the multi-part floating lid to deform so that a center portion of the multi-part floating lid has moved upwardly through an aperture formed in the lid-retainer ring;

FIG. 9B is a view similar to FIG. 8B after the tray has moved into the oven to heat each of the nine canisters and an enlarged perspective view of the canister that was singled out in FIG. 8B showing that heat and pressure inside the canister have caused the center portion of the multi-part floating lid to expand and move upwardly through the aperture in the lid-retainer lid and the canister and that food products have been sterilized by the heat and pressure without bursting or damaging the canister;

FIG. 10A is a view similar to FIGS. 8A and 9A of the canister after it has been moved out of the oven as suggested in FIG. 10B and the canister has cooled so that pressure inside the canister has decreased causing the multi-part floating lid to deform so that the center portion has moved downwardly through the open mouth of the container;

FIG. 10B is a view similar to FIGS. 8B and 9B after the tray has moved out of the oven and an enlarged perspective view of the canister that was singled out in FIGS. 8B and 9B showing that the canister has cooled and the pressure inside the canister has decreased to cause the multi-part floating lid to deform so that the center portion of the multi-part floating lid has moved downwardly through the open mouth of the container;

FIG. 11 is an enlarged sectional view similar to FIG. 3 showing the lid-retainer ring coupled to the filler neck included in the container to trap the multi-part floating lid between the lid-retainer ring and the filler neck so that the open mouth formed in the container is closed;

FIG. 12 is an enlarged partial view of the circled region of FIG. 11 showing that the lid-retainer support retains the multi-part floating lid in the lid-retainer cavity and that the multi-part lid is trapped between the lid-retainer ring and the filler neck such that the elastic barrier film and the disk of the multi-part floating lid close the open mouth included in the filler neck and the gasket of the multi-part floating lid engages the brim of the filler neck to block egress of food products out of and ingress of contaminants into the product-storage region formed in the container;

FIG. 13 is a partial perspective view of another embodiment of a canister in accordance with the present disclosure showing that the canister includes a container and a closure coupled to the container and that portions of the canister have been broken away to reveal that the closure includes an outer lid-retainer ring configured to mate with the container and an inner multi-part floating lid trapped between the lid-retainer ring and the container to close an open mouth formed in the container;

FIG. 14 is an exploded perspective assembly view of the canister of FIG. 13 showing that the container includes a filler neck coupled to an underlying body and formed to include an open mouth and showing that the closure includes, from top to bottom, a lid-retainer ring configured to be tightened onto a container filler neck to trap a multi-part floating lid between the lid-retainer ring and the container, a multi-part floating lid for closing an open mouth of the filler neck and showing that the multi-part floating lid includes an elastic barrier film, a lid-reinforcing core, and a gasket and showing that the lid-reinforcing core is an annular band;

FIG. 15 is a sectional view taken along line 15-15 of FIG. 13 showing the closure tightened on the filler neck of the container to restrict movement of the multi-part floating lid and to close the open mouth included in the filler neck so that food products stored in the container are blocked from escaping the container through the open mouth;

FIG. 16 is an enlarged view of the circled region of FIG. 15 showing that the lid-retainer ring is formed to include a lid-retainer cavity and that the lid-retainer ring includes a top wall, a side wall extending downwardly to mate with the container, and a lid-retainer support that retains the multi-part floating lid in the lid-retainer cavity and showing that the gasket included in the multi-part floating lid engages a brim included in the filler neck of the container to block egress food products and ingress of contaminants from between the container and the closure;

FIG. 17 is an exploded assembly view of the enlarged partial view of the canister of FIG. 16 showing the assembled multi-part floating lid in spaced-apart relation between the lid-retainer ring and the filler neck of the container and suggesting that the gasket engages the brim of the container;

FIG. 18 is an exploded assembly view of the multi-part floating lid of FIG. 17 showing that the multi-part floating lid includes, from top to bottom, an elastic barrier film formed to mate with an upper surface of an underlying annular band, an annular band, and a gasket and showing that the annular band is monolithic and includes a radial band body including the upper surface and an opposite lower surface and a downwardly extending gasket-receiving track appended to the inner surface of the band body at an outer-band edge of the annular band and sized to receive the gasket therein as suggested in FIG. 17;

FIGS. 19A-21B are a series of views showing the canister of FIGS. 13-15 undergoing a high-temperature sterilization process known as retort;

FIG. 19A is a sectional view similar to FIG. 15 of a canister on a conveyer moving toward an oven to undergo retort as suggested in FIG. 19B and showing that the canister has not entered the oven and, as such, the multi-part floating lid is un-deformed;

FIG. 19B is a diagrammatic view of a tray carrying nine canisters in accordance with the present disclosure and moving along the conveyor toward the oven to undergo retort and an enlarged perspective view of one of those canisters before it is heated and pressurized in the oven;

FIG. 20A is a view similar to FIG. 19A of the canister after it has been moved into the oven as suggested in FIG. 20B and showing that the canister is heated and pressurized within the oven to sterilize the canister and food products stored within the canister and that the heat and pressure inside the canister have caused the multi-part floating lid to deform so that a center portion of the multi-part floating lid has moved upwardly through an aperture formed in the lid-retainer ring;

FIG. 20B is a view similar to FIG. 19B after the tray has moved into the oven to heat each of the nine canisters and an enlarged perspective view of the canister that was singled out in FIG. 19B showing that heat and pressure inside the canister have caused the center portion of the multi-part floating lid to expand and move upwardly through the aperture in the lid-retainer lid and the canister and that food products have been sterilized by the heat and pressure without bursting or damaging the canister;

FIG. 21A is a view similar to FIGS. 19A and 19A of the canister after it has been moved out of the oven as suggested in FIG. 21B and the canister has cooled so that pressure inside the canister has decreased causing the multi-part floating lid to deform so that the center portion has moved downwardly through the open mouth of the container; and FIG. 21B is a view similar to FIGS. 19B and 20B after the tray has moved out of the oven and an enlarged perspective view of the canister that was singled out in FIGS. 19B and 20B showing that the canister has cooled and the pressure inside the canister has decreased to cause the multi-part floating lid to deform so that the center portion of the multi-part floating lid has moved downwardly through the open mouth of the container.

DETAILED DESCRIPTION

A canister 10 in accordance with the present disclosure is shown, for example, in FIGS. 1-4 and 8B-10B. Canister 10 includes a container 12 formed to include a product-storage region 22 configured to store products (e.g., food products) therein and a closure 14 as shown in FIGS. 1-4. Closure 14 may be separated from container 12 to allow access to product-storage region 22 through an open mouth 20 formed in container 12 as suggested in FIG. 2. Closure 14 may be coupled to container 12 to close open mouth 20 and block access to product-storage region 22 as shown in FIGS. 1, 3, and 4. Closure 14 is configured to deform and survive, without rupturing, a high temperature sterilization process known as retort as suggested in FIGS. 8B, 9B, and 10B.

Closure 14 includes a lid-retainer ring 16 and a multi-part floating lid 18 as shown in FIGS. 2-4. Lid-retainer ring 16 couples multi-part floating lid 18 to container 12 to block access to product-storage region 22 and minimize force required to separate closure 14 from container 12 after canister 10 has been through the retort process. Multi-part floating lid 18 is configured to deform during and after the retort process to minimize pressure in product-storage region 22. Prior to retort, closure 14 has a pre-retort shape as shown, for example, in FIGS. 1, 3, 4, 8A, and 8B. During retort, canister 10 is exposed to high temperatures which cause pressure in product-storage region 22 to increase so that closure 14 deforms outwardly to assume a retort shape as shown in FIGS. 9A and 9B. After retort, canister 10 cools and closure 14 deforms inwardly to assume a post-retort shape as shown in FIGS. 10A and 10B.

Multi-part floating lid 18 of closure 14 includes, from top to bottom as shown in FIG. 2, an elastic barrier film 24, a lid-reinforcing core 26, and gasket 28. Elastic barrier film 24 is coupled to an outer surface 38 of lid-reinforcing core 26 and is configured to block communication of oxygen through multi-part floating lid 18 when closure 14 is coupled to container 12 as shown in FIGS. 1, 3, and 4. Gasket 28 is coupled to an inner surface 40 of lid-reinforcing core 26 and is configured to block ingress of contamination into product-storage region 22 and egress of products stored out of product-storage region 22 when closure 14 is coupled to container 12. Lid-reinforcing core 26 is located between elastic barrier film 24 and gasket 28 and configured to provide means for supporting elastic barrier film 24 during deformation of closure 14 between the pre-retort, retort, and post-retort shapes so that risk of damage to closure 14 is minimized during retort and for minimizing risk of forming an opening in closure 14 in response to an unintended cut or poke to elastic barrier film 24 so that open mouth 20 remains closed when closure 14 is coupled to container 12. In some embodiments, lid-reinforcing core 26 is a disk 26, as shown, for example, in FIGS. 1-12. In other embodiments, lid-reinforcing core 26 is an annular band 326, as shown, for example, in FIGS. 13-21B.

Canister 10 includes container 12 and closure 14 as shown in FIG. 1. Container 12 includes a body 84 and a filler neck 88 coupled to body 84 as shown in FIG. 2. Body 84 and filler neck 88 cooperate to define product-storage region 22.

Filler neck 88 of container 12 includes a brim 122, a neck wall 86, and neck threads 120 as shown in FIG. 2. Brim 122 is configured to mate with multi-part floating lid 18 as shown in FIG. 3. Neck wall 86 extends downwardly from brim 122 and is coupled to body 84 of container 12. Brim 122 and neck wall 86 are, for example, annular and cooperate to define open mouth 20 which opens into product-storage region 22. Neck threads 120 are coupled to neck wall 86 and arranged to extend outwardly away from both neck wall 86 and open mouth 20. Neck threads 120 cooperate with closure threads 124 included in lid-retainer ring 16 of closure 14 to cause closure 14 to be coupled selectively to filler neck 88.

Closure 14 couples to filler neck 88 to close open mouth 20 as shown in FIG. 3. Closure 14 includes lid-retainer ring 16 and multi-part floating lid 18 as shown in FIG. 2. Lid-retainer ring 16 is configured to trap multi-part floating lid 18 between lid-retainer ring 16 and filler neck 88 when closure 14 is mated with container 12 as shown in FIGS. 3 and 4. Multi-part floating lid 18 is configured to block the escape of products stored within product-storage region 22 of canister 10 when closure 14 is mated with container 12.

Multi-part floating lid 18 is trapped in an interior region 56 formed in lid-retainer ring 16 as shown in FIGS. 4, 11, and 12. Multi-part floating lid 18 includes elastic barrier film 24, lid-reinforcing core 26, and gasket 28 as shown in FIGS. 2 and 7. In the illustrative embodiment, lid-reinforcing core 26 is disk 26. Disk 26 blocks escape of products stored in product-storage region 22 through open mouth 20 and provides means for supporting elastic barrier film 24 during deformation of closure 14 between the pre-retort, retort, and post-retort shapes so that risk of damage to closure 14 is minimized. Elastic barrier film 24 blocks communication of oxygen stored in product-storage region 22 through disk 26.

Gasket 28 is coupled to disk 26 to minimize communication of fluids between product-storage region 22 and atmosphere surrounding canister 10.

Disk 26 includes a disk body 30 sized to close open mouth 20 when disk 26 is trapped between lid-retainer ring 16 and container 12, an annular disk-support ring 32 coupled to disk body 30 to cause disk 26 to resist deformation, and a gasket-receiving track 34 coupled to disk body 30 to locate gasket 28 between lid-retainer ring 16 and container 12 as shown in FIGS. 5 and 6. In one illustrative example, disk 26 is monolithic and made from polyurethane.

Disk body 30 includes an upwardly facing outer surface 38 arranged to face away from container 12, a downwardly facing inner surface 40 arranged to face opposite outer surface 38, and a perimeter edge 42 arranged to extend between and interconnect inner and outer surfaces 40, 38 as shown in FIG. 6. Elastic barrier film 24 is coupled to outer surface 38 of disk 26. In one illustrative example, elastic barrier film 24 is coupled to disk 26 during an in-mold labeling process in which elastic barrier film 24 is placed in a mold cavity prior to injection of plastics materials into the mold cavity to establish disk 26. Heat from the molten plastics materials causes elastic barrier film 24 to bond to disk 26 as the plastics materials cools and solidifies.

Annular disk-support ring 32 is appended to the downwardly facing inner surface 40 and spaced apart radially from perimeter edge 42 as shown in FIG. 6. Annular disk-support ring 32 has, for example, a circular shape and extends downwardly away from inner surface 40. Annular disk-support ring 32 supports elastic barrier film 24 during deformation of closure 14 between the pre-retort, retort, and post-retort shapes.

Gasket-receiving track 34 is appended to the downwardly facing inner surface 40 at perimeter edge 42 and is arranged to extend radially inward toward annular disk-support ring 32 as shown in FIG. 6. Gasket-receiving track 34 extends downwardly away from inner surface 40. Gasket-receiving track 34 is sized to receive gasket 28 therein and is arranged to locate gasket 28 between lid-retainer ring 16 and container 12 so that gasket 28 engages brim 122 included in container 12 when closure 14 is tightened fully onto container 12.

Disk 26 has a disk thickness 26T as shown in FIG. 6. In the illustrative embodiment, disk thickness 26T is about 0.025 inches (0.635 millimeters). In the illustrative embodiment, disk 26 has a disk diameter 26D. Disk diameter 26D is sized to both cover open mouth 20 and fit inside interior region 56 of lid-retainer ring 16. In the illustrative embodiment, disk diameter 26D is about 2.48 inches (63 millimeters).

Elastic barrier film 24 is coupled to outer surface 38 of disk 26 as shown in FIGS. 5-7. Elastic barrier film 24 includes an outer surface 94, an inner surface 96 spaced apart and opposite outer surface 94, and a perimeter edge 92 as shown in FIGS. 5 and 6. Outer surface 94 is arranged to face away from disk 26 as shown in FIG. 6. Inner surface 96 is arranged to face opposite outer surface 94 toward outer surface 38 of disk 26. Perimeter edge 92 is arranged to extend between and interconnect inner and outer surfaces 96, 98 of elastic barrier film 24.

Elastic barrier film 24 has a film thickness 24T as shown in FIG. 6. In the illustrative embodiment, film thickness 24T is about 0.005 inches (0.127 millimeters). In the illustrative embodiment, elastic barrier film 24 has a film diameter 24D. Film diameter 24D is sized to cover outer surface 38 and perimeter edge 42 of disk 26. In the illustrative embodiment, film diameter 24D is about 2.48 inches (63 millimeters).

Elastic barrier film 24 is comprised, for example, of a number of layers. As shown in FIG. 7, elastic barrier film 24 includes, from outer surface 94 to inner surface 96, polypropylene layer 98A, tie layer 98B, nylon layer 98C, EVOH layer 98D, nylon layer 98E, EVOH layer 98F, nylon layer 98G, tie layer 98H, and polypropylene layer 98I, in some embodiments. Any one of EVOH layers 98D, 98F of elastic barrier film 24 may act as an oxygen-barrier layer. In other example, elastic barrier film 24 may include one or more layers configured to act as an oxygen barrier as well as various other layers which may be chosen depending on the desired function of the canister.

Figure 7A:
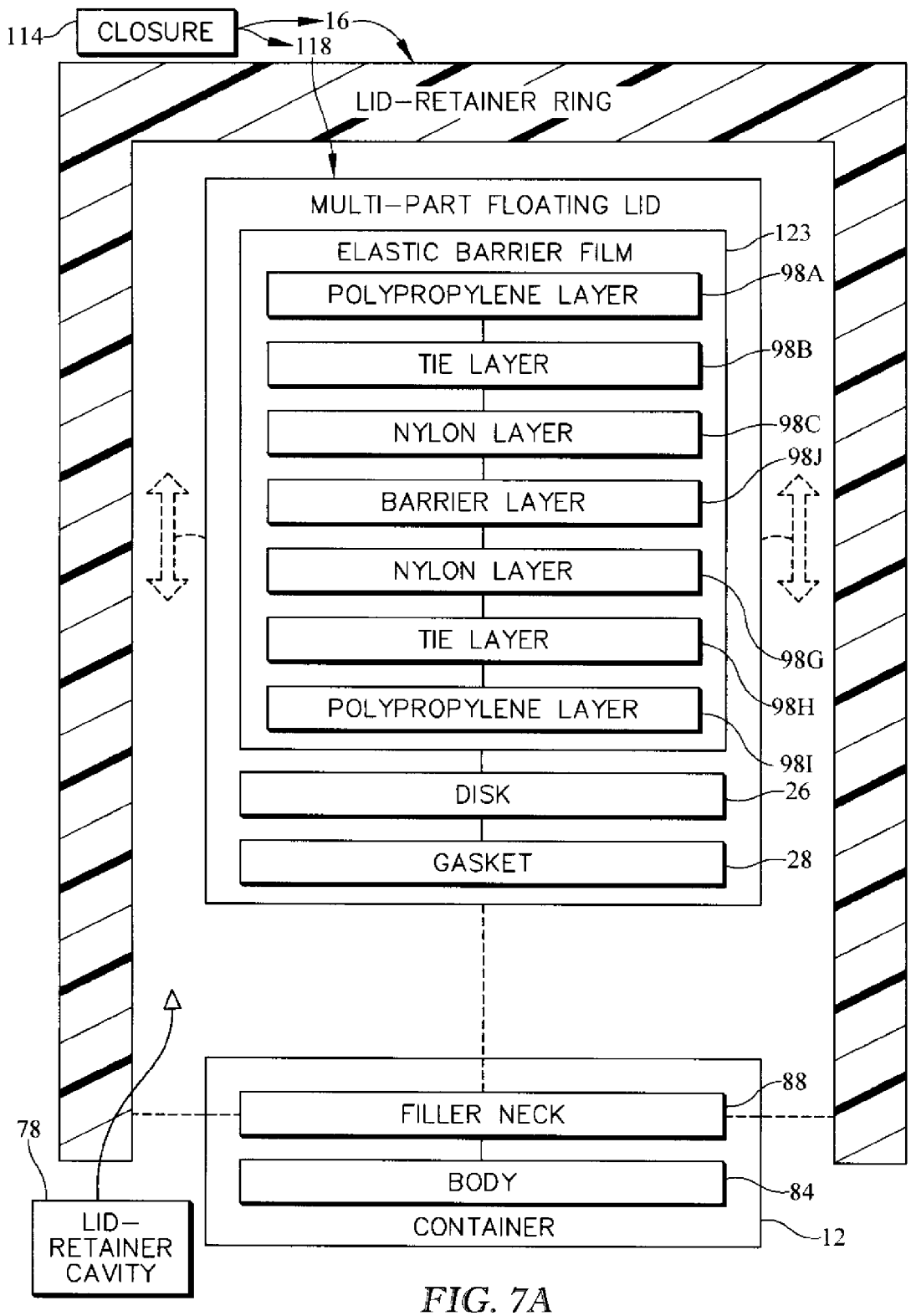

Another embodiment of a closure 114 is shown for example in FIG. 7A. Closure 114 includes lid-retainer ring 16 and a multi-part floating lid 118. Multi-part floating lid 118 includes an elastic barrier film 123, disk 26, and gasket 28 as shown in FIG. 7A. Elastic barrier film 123 includes, from top to bottom, polypropylene layer 98A, tie layer 98B, nylon layer 98C, a barrier layer 98J, nylon layer 98G, tie layer 98H, and polypropylene layer 98I. In one example, barrier layer 98J is an EVOH layer. In another example, barrier layer 98J is a metallic layer. In another example, barrier layer 98J is a polyester layer with a metal oxide coating. In yet another example, barrier layer 98J is a multilayer structure comprising one or more of the EVOH layer, metallic layer, polyester layer with a metal oxide coating, any other suitable alternative, or any other suitable combination.

In still yet another embodiment, an elastic barrier film used in a multi-part floating lid in accordance with the present disclosure includes a nylon layer, an adhesive layer, a first polypropylene layer, a first tie layer, an EVOH layer, a second tie layer, and a second polypropylene layer. In still yet another embodiment, an elastic barrier film includes a polyethylene terephthalate layer, an adhesive layer, a polypropylene layer, a tie layer, an EVOH layer, a tie layer, and a polypropylene layer. In another embodiment, an elastic barrier film includes a nylon layer, an adhesive layer, an AlOx coated polyethylene terephthalate layer, an adhesive layer, a polypropylene layer, a tie layer, a nylon layer, a tie layer, and a polypropylene layer. In yet another embodiment, an elastic barrier film includes an AlOx coated polyethylene terephthalate layer, and adhesive layer, a nylon layer, an adhesive layer, a polypropylene layer, a tie layer, a nylon layer, a tie layer, and a polypropylene layer.

An elastic barrier film in accordance with the present disclosure includes one or more layers. In one example, the elastic barrier film includes a first layer, a second layer spaced apart from the first layer, and a barrier layer located therebetween. The first layer may be made from polypropylene, nylon, polyethylene terephthalate, combinations of the foregoing, or any other suitable material. The second layer may be made from polyethylene so as to bond with containers made from polyethylene. However, any other suitable material may be used for the second layer. The barrier layer may be an EVOH layer, a metallic layer, an AlOx coated polyethylene terephthalate layer, or any other suitable materials. In another example, the barrier layer may include one or more sub-layers which may include an EVOH layer, a metallic layer, an AlOx coated polyethylene terephthalate layer, one or more tie layers, one or more adhesive layers, and combinations of the foregoing.

In yet another example, the elastic barrier film may further includes an ink layer. The ink layer may be printed on the first layer so that the ink layer is visible to a consumer. In one example, the ink layer may be printed an inner surface of the first layer which is arranged to face toward the barrier layer.

In another example, the ink layer may be printed on an outer surface arranged to face away from the barrier layer.

Gasket 28 is coupled to disk 26 as shown in FIGS. 2, 6, 7, and 11-12. Gasket 28 blocks egress of products and fluids stored out of product-storage region 22 and ingress of contaminants into product-storage region 22 where multi-part floating lid 18 contacts filler neck 88. Gasket 28 may be made from rubber or any other suitable seating material.

Gasket 28 includes an upper-gasket surface 104, a lower-gasket surface 108, an inner-gasket edge 102, and an outer-gasket edge 106 as shown in FIG. 6. Upper-gasket surface 104 is arranged to face toward inner surface 40 of disk 26. Lower-gasket surface 108 is arranged to lie in spaced-apart relation to upper-gasket surface 104 and face toward brim 122 opposite upper-gasket surface 104. Inner-gasket edge 102 is arranged to extend between and interconnect upper-gasket surface 104 and lower-gasket surface 108. Outer-gasket edge 106 is arranged to lie in spaced-apart relation to inner-gasket edge 102 and to extend between and interconnect upper-gasket surface 104 and lower-gasket surface 108. In one illustrative example, upper-gasket surface 104 is spaced apart from lower-gasket surface 108 such that gasket 28 has a gasket thickness 28T of about 0.040 inches (1.016 millimeters).

In the illustrative embodiment, gasket 28 is ring-shaped. As shown in FIG. 6, inner-gasket edge 102 is spaced apart from a closure axis 70 a first radial distance 72. Outer-gasket edge 106 is spaced apart from closure axis 70 a relatively greater second radial distance 74 as shown in FIG. 6. First radial distance 72 is about 1.004 inches (25.5 millimeters) and second radial distance 74 is about 1.240 inches (31.5 millimeters). As a result, gasket 28 had a radial width 76 of about 0.236 inches (6 millimeters) as shown in FIG. 6. Upper-gasket surface 104 is located in gasket-receiving track 34 and coupled to inner surface 40 of disk 26 as shown in FIGS. 5, 10, and 11. In another illustrative example, a gasket in accordance with the present disclosure may be a continuous sheet and omit an inner gasket edge.

Canister 10 is configured to survive a high temperature and high-pressure sterilization process known as retort without rupturing as suggest in FIGS. 8B-10B. Food products are stored within container 12 and closure 14 is tightened fully to container 12 to contain the food products in canister 10. Prior to retort, disk 26 is approximately flat. Canister 10 is then heated in an oven 48 to sterilize canister 10 and the food products.

During retort, the temperature and pressure inside canister 10 increases. The increased pressure applies an outward force 50 to canister 10, including multi-part floating lid 18, as suggested in FIG. 9A. Outward force 50 causes a center portion 128 of disk 26 to deform and move upwardly as shown in FIGS. 9A and 9B. Container 12 and closure 14 cooperate to minimize risk of canister 10 rupturing as outward force 50 is applied to canister 10.

After retort, canister 10 is allowed to cool as suggested in FIG. 10B. Gas within product-storage region 22 of canister 10 cools and becomes denser and the pressure within product-storage region 22 of canister 10 decreases. The decreased pressure causes the ambient air surrounding canister 10 to apply an inward force 52 to canister 10. Inward force 52 causes disk 26 to deform such that center portion 128 of disk 26 moves downwardly into container 12 as shown in FIGS. 10A and 10B.

Prior to retort, products are located in product-storage region 22 of canister 10 and closure 14 is mated with filler neck 88. Product-storage region 22 of canister 10 has a pre-retort temperature 130T, pressure 130P, and volume 130V as suggested below the enlarged perspective view of canister 10 in FIG. 9B. In the illustrative embodiment, pre-retort temperature 130T and pressure 130P are about equal to atmospheric temperature and pressure. Pre-retort volume 130V is defined by container 12 and closure 14. Prior to retort, multi-part floating lid 18 has a floating lid pre-retort shape where multi-part floating lid 18 is about flat and lies in horizontal plane 90 as shown in an enlarged perspective view of canister 10 in FIG. 11.

During retort, a number of canisters 10 are placed on a tray and moved along a conveyer toward oven 48 as shown in FIG. 8B. As canister 10 progresses along the conveyer, canister 10 is moved into oven 48 as shown in FIG. 9B. Oven 48 applies heat 126 to canister 10 to increase the temperature of product-storage region 22 until it reaches a retort temperature 132T that is greater than pre-retort temperature 130T. As an example, retort temperature 132T is about 260 degrees Fahrenheit (126.67 degrees Celsius).

Container 12 and closure 14 initially remain undeformed as the temperature of product-storage region 22 is below retort temperature 132T. Under the ideal gas law, an increase in temperature causes an increase in pressure, if volume is held constant. As such, the increased temperature causes pressure 132P of product-storage region 22 to increase such that product-storage region 22 has a retort pressure 132P that is greater than pre-retort pressure 130P as suggested below the enlarged perspective view of canister 10 in FIG. 9B. As an example, retort pressure 132P is about 15-35 pounds per square inch.

As the temperature of product-storage region 22 reaches retort temperature 132T, disk 26 and elastic barrier film 24 deform elastically due to the higher retort temperature 132T and pressure 132P applied to disk 26 and elastic barrier film 24 as shown in FIG. 9A. As such, multi-part floating lid 18 assumes a floating lid retort shape as shown in the enlarged perspective view of canister 10 in FIG. 9B.

Gasket 28 remains mated with brim 122 of filler neck 88 while canister 10 is in oven 48 and disk 26 and elastic barrier film 24 are expanded. As such, product-storage region 22 remains substantially sealed off from the atmosphere along with any products received within product-storage region 22 of canister 10. The pressure of product-storage region 22 may surpass retort pressure 132P such that it breaks the seal allowing some of the air, or other gasses, sealed inside canister 10 to escape between gasket 28 and brim 122 until the pressure of product-storage region 22 is reduced to retort pressure 132P and the seal is reestablished. Once the seal is reestablished, less air or other gasses are stored within product-storage region 22.

As the conveyer moves canister 10 out of oven 48, canister 10 cools to an ambient temperature as suggested in FIG. 10B. Once cooled, product-storage region 22 has a post-retort temperature 134T, pressure 134P, and volume 130V, as suggested below the enlarged perspective view of canister 10 in FIG. 10B. Post-retort temperature 134T of product-storage region 22 is similar to pre-retort temperature 130T of product-storage region 22 because the ambient temperature outside of oven 48 is similar before and after oven 48. Post-retort pressure 134P and volume 134V of product-storage region are less than pre-retort pressure 130P and volume 130V of product-storage region 22 due to air or other gasses escaping canister 10 when canister 10 was heated in oven 48.

As canister 10 cools, the pressure of product-storage region 22 is reduced. Disk 26 and elastic barrier film 24 deform as the pressure of product-storage region 22 reduces to post-retort pressure 134P. Multi-part floating lid 18 assumes the approximately pre-retort shape as disk 26 and elastic barrier film 24 contract.

Post-retort pressure 134P is less than pre-retort pressure 130P due to air escaping while canister 10 is in oven 48. The ambient pressure outside of canister 10 is higher than post-retort pressure 134P of product-storage region 22 and the ambient pressure applies inward force 52 on disk 26 and elastic barrier film 24 to cause disk 26 and elastic barrier film 24 to deform elastically and depress such that center portion 128 of multi-part floating lid 18 depresses into open mouth 20 as shown in FIGS. 10A and 10B. As such, multi-part floating lid 18 assumes the post-retort shape when product-storage region 22 reaches post-retort temperature 134T and pressure 134P. The depression of disk 26 and elastic barrier film 24 reduces the volume of product-storage region 22 such that product-storage region 22 has a post-retort volume 134V that is less than pre-retort volume 130V.

After the seal is first broken during removal of closure 14 from container 12, disk 26 and elastic barrier film 24 contract and multi-part floating lid 18 resumes an approximately pre-retort shape. As such, the depressed post-retort shape of multi-part floating lid 18 may be an indication that canister 10 has both been through the retort process and the seal between multi-part floating lid 18 and filler neck 88 has not been broken. Such post-retort shape provides a tamper-evident feature to the consumer.

Lid-retainer ring 16 is configured to trap multi-part floating lid 18 between lid-retainer ring 16 and filler neck 88 when closure 14 is mated with container 12 as shown in FIGS. 11 and 12. Lid-retainer ring 16 includes a top wall 46 and an annular side wall 54 coupled to top wall 46 and arranged to extend downwardly from top wall 46 as shown in FIG. 5. Top wall 46 and annular side wall 54 are formed to define an interior region 56 of lid-retainer ring 16. An upper aperture 58 is formed in top wall 46 and arranged to open into interior region 56. A lower aperture 60 is formed to lie in spaced-apart relation spaced apart from upper aperture 58 and arranged to open into interior region 56. As shown in FIG. 11, lower aperture 60 is defined by annular side wall 54. When closure 14 is coupled to container 12, filler neck 88 of container 12 is arranged to extend through lower aperture 60 and into interior region 56. Lower aperture 60 is also sized to receive multi-part floating lid 18 there through.

Annular side wall 54 of lid-retainer ring 16 includes an inner surface 62 and an outer surface 64 as shown in FIGS. 11 and 12. Inner surface 62 includes closure threads 124 and a lid-retainer support 68. Closure threads 124 extend inwardly into interior region 56. Closure threads 124 are formed to mate with neck threads 120 included in filler neck 88 to couple closure 14 to filler neck 88 when closure 14 is rotated about closure axis 70 in a clockwise direction. Closure threads 124 and neck threads 120 cooperate to separate closure 14 from filler neck 88 when closure 14 is rotated about closure axis 70 in a counter-clockwise direction. Lid-retainer support 68 is, for example, an annular flange that extends inwardly away from annular side wall 54 towards interior region 56 as shown in FIGS. 11 and 12.

Top wall 46, annular side wall 54, and lid-retainer support 68 cooperate to define a lid-retainer cavity 78. In the illustrative embodiment, multi-part floating lid 18 is trapped between top wall 46, annular side wall 54, and lid-retainer support 68 to block multi-part floating lid 18 from escaping lid-retainer cavity 78. In the illustrative embodiment, top wall 46, annular side wall 54, and lid-retainer support 68 cooperate to allow limited movement of multi-part floating lid 18 vertically, horizontally, radially, or any combination thereof in lid-retainer cavity 78. During removal of closure 14 from container 12, lid-retainer support 68 engages multi-part floating lid 18 and operates to pry closure 14 away from brim 122 so that removal of closure 14 is simplified.

Another embodiment of a canister 310, in accordance with the present disclosure, including a multi-part floating lid 318 in which lid-reinforcing core 26 is annular band 326, is shown, for example, in FIGS. 13-21B. Canister 310 includes a closure 314 and container 12. Closure 314 includes lid-retainer ring 16 and multi-part floating lid 318, as shown in FIGS. 13-16.

Multi-part floating lid 318 includes elastic barrier film 24, annular band 326, and gasket 28 as shown in FIGS. 14 and 16-18. Annular Band 326 provides means for supporting elastic barrier film 24 during deformation of closure 314 between the pre-retort, retort, and post-retort shapes so that risk of damage to closure 314 is minimized. Elastic barrier film 24 blocks escape of products stored in product-storage region 22 and any communication of oxygen stored in product-storage region 22 through open mouth 20. Gasket 28 is coupled to annular band 326 to minimize communication of fluids between product-storage region 22 and atmosphere surrounding canister 10.

Annular band 326 includes a band body 330 sized to close open mouth 20 when annular band 326 is trapped between lid-retainer ring 16 and container 12 and a gasket-receiving track 34 coupled to band body 330 to locate gasket 28 between lid-retainer ring 16 and container 12 as shown in FIGS. 17 and 18. In one illustrative example, annular band 326 is monolithic and made from polyurethane.

Band body 330 includes an upwardly facing outer surface 338 arranged to face away from container 12, a downwardly facing inner surface 340 arranged to face opposite outer surface 338, an inner-band edge 402, and an outer-band edge 406 as shown in FIG. 18. Outer surface 338 is arranged to face toward inner surface 96 of elastic barrier film 24. Inner surface surface 340 is arranged to lie in spaced-apart relation to outer surface 338 and face toward brim 122 opposite outer surface 338. Inner-band edge 402 is arranged to extend between and interconnect outer surface 338 and inner surface 340. Outer-band edge 406 is arranged to lie in spaced-apart relation to inner-band edge 402 and to extend between and interconnect outer surface 338 and inner surface 340.

Elastic barrier film 24 is coupled to outer surface 338 of annular band 326. In one illustrative example, elastic barrier film 24 is coupled to annular band 326 during an in-mold labeling process in which elastic barrier film 24 is placed in a mold cavity prior to injection of plastics materials into the mold cavity to establish annular band 326. Heat from the molten plastics materials causes elastic barrier film 24 to bond to annular band 326 as the plastics materials cools and solidifies.

Gasket-receiving track 34 is appended to the downwardly facing inner surface 340 at outer-band edge 406 and is arranged to extend radially inward toward closure axis 70 as shown in FIG. 18. Gasket-receiving track 34 extends downwardly away from inner surface 340. Gasket-receiving track 34 is sized to receive gasket 28 therein and is arranged to locate gasket 28 between lid-retainer ring 16 and container 12 so that gasket 28 engages brim 122 included in container 12 when closure 314 is tightened fully onto container 12.

Annular band 326 has a band thickness 326T as shown in FIG. 18. In the illustrative embodiment, band thickness 326T is about 0.025 inches (0.635 millimeters). In illustrative embodiments, inner-band edge 402 is spaced apart from a closure axis 70 a first radial distance 372. Outer-band edge 406 is spaced apart from closure axis 70 a relatively greater second radial distance 374 as shown in FIG. 18. First radial distance 372 is about 1.004 inches (25.5 millimeters) and second radial distance 374 is about 1.240 inches (31.5 millimeters). As a result, annular band 326 had a radial width 376 of about 0.236 inches (6 millimeters) as shown in FIG. 18.

Elastic barrier film 24 is coupled to outer surface 338 of annular band 326 as shown in FIGS. 17 and 18. Elastic barrier film 24 includes outer surface 94, inner surface 96 spaced apart and opposite outer surface 94, and perimeter edge 92. Outer surface 94 is arranged to face away from annular band 326 as shown in FIG. 18. Inner surface 96 is arranged to face opposite outer surface 94 toward outer surface 338 of annular band 326. Perimeter edge 92 is arranged to extend between and interconnect inner and outer surfaces 96, 98 of elastic barrier film 24.

Elastic barrier film 24 has a film thickness 24T as shown in FIG. 18. In the illustrative embodiment, film thickness 24T is about 0.005 inches (0.127 millimeters). In the illustrative embodiment, elastic barrier film 24 has a film diameter 24D. Film diameter 24D is sized to cover outer surface 338 of annular band 326. In the illustrative embodiment, film diameter 24D is about 2.48 inches (63 millimeters).

Gasket 28 is coupled to annular band 326 as shown in FIG. 17. Gasket 28 blocks egress of products and fluids stored out of product-storage region 22 and ingress of contaminants into product-storage region 22 where multi-part floating lid 318 contacts filler neck 88. Gasket 28 may be made from rubber or any other suitable seating material.

Gasket 28 includes upper-gasket surface 104, lower-gasket surface 108, inner-gasket edge 102, and outer-gasket edge 106 as shown in FIG. 18. Upper-gasket surface 104 is arranged to face toward inner surface 340 of annular band 326. Lower-gasket surface 108 is arranged to lie in spaced-apart relation to upper-gasket surface 104 and face toward brim 122 opposite upper-gasket surface 104. Inner-gasket edge 102 is arranged to extend between and interconnect upper-gasket surface 104 and lower-gasket surface 108. Outer-gasket edge 106 is arranged to lie in spaced-apart relation to inner-gasket edge 102 and to extend between and interconnect upper-gasket surface 104 and lower-gasket surface 108. In one illustrative example, upper-gasket surface 104 is spaced apart from lower-gasket surface 108 such that gasket 28 has a gasket thickness 28T of about 0.040 inches (1.016 millimeters).

Gasket 28 is ring-shaped, as shown in FIG. 14. Inner-gasket edge 102 is spaced apart from a closure axis 70 a first radial distance 72, as shown in FIG. 18. Outer-gasket edge 106 is spaced apart from closure axis 70 a relatively greater second radial distance 74 as shown in FIG. 18. First radial distance 72 is about 1.004 inches (25.5 millimeters) and second radial distance 74 is about 1.240 inches (31.5 millimeters). As a result, gasket 28 had a radial width 76 of about 0.236 inches (6 millimeters) as shown in FIG. 18. Upper-gasket surface 104 is located in gasket-receiving track 334 and coupled to inner surface 340 of annular band 326 as shown in FIG. 17.

Canister 310 is configured to survive a high temperature and high-pressure sterilization process known as retort without rupturing as suggest in FIGS. 19B-21B. Food products are stored within container 12 and closure 314 is tightened fully to container 12 to contain the food products in canister 310. Prior to retort, elastic barrier film 24 is approximately flat. Canister 310 is then heated in an oven 48 to sterilize canister 310 and the food products.

During retort, the temperature and pressure inside canister 310 increases. The increased pressure applies an outward force 50 to canister 310, including multi-part floating lid 318, as suggested in FIG. 20A. Outward force 50 causes a center portion 428 of elastic barrier film 24 to deform and move upwardly as shown in FIGS. 20A and 20B. Container 12 and closure 314 cooperate to minimize risk of canister 310 rupturing as outward force 50 is applied to canister 310.

After retort, canister 310 is allowed to cool as suggested in FIG. 21B. Gas within product-storage region 22 of canister 310 cools and becomes denser and the pressure within product-storage region 22 of canister 310 decreases. The decreased pressure causes the ambient air surrounding canister 310 to apply an inward force 52 to canister 310. Inward force 52 causes elastic barrier film 24 to deform such that center portion 428 of elastic barrier film 24 moves downwardly into container 12 as shown in FIGS. 21A and 21B.

Prior to retort, products are located in product-storage region 22 of canister 310 and closure 314 is mated with filler neck 88. Product-storage region 22 of canister 310 has a pre-retort temperature 430T, pressure 430P, and volume 430V as suggested below the enlarged perspective view of canister 310 in FIG. 20B. In the illustrative embodiment, pre-retort temperature 430T and pressure 430P are about equal to atmospheric temperature and pressure. Pre-retort volume 430V is defined by container 12 and closure 314. Prior to retort, multi-part floating lid 318 has a floating lid pre-retort shape where multi-part floating lid 318 is about flat and lies in horizontal plane 90.

During retort, a number of canisters 310 are placed on a tray and moved along a conveyer toward oven 48 as shown in FIG. 19B. As canister 310 progresses along the conveyer, canister 310 is moved into oven 48 as shown in FIG. 20B. Oven 48 applies heat 126 to canister 310 to increase the temperature of product-storage region 22 until it reaches a retort temperature 432T that is greater than pre-retort temperature 430T. As an example, retort temperature 432T is about 260 degrees Fahrenheit (126.67 degrees Celsius).

Container 312 and closure 314 initially remain undeformed as the temperature of product-storage region 22 is below retort temperature 432T. Under the ideal gas law, an increase in temperature causes an increase in pressure, if volume is held constant. As such, the increased temperature causes pressure 432P of product-storage region 22 to increase such that product-storage region 22 has a retort pressure 432P that is greater than pre-retort pressure 430P as suggested below the enlarged perspective view of canister 310 in FIG. 20B. As an example, retort pressure 432P is about 15-35 pounds per square inch.

As the temperature of product-storage region 22 reaches retort temperature 432T, elastic barrier film 24 deforms elastically due to the higher retort temperature 432T and pressure 432P applied to elastic barrier film 24, as shown in FIG. 20A. As such, multi-part floating lid 318 assumes a floating lid retort shape as shown in the enlarged perspective view of canister 310 in FIG. 20B.

Gasket 28 remains mated with brim 122 of filler neck 88 while canister 310 is in oven 48 and elastic barrier film 24 is expanded. As such, product-storage region 22 remains substantially sealed off from the atmosphere along with any products received within product-storage region 22 of canister 310. The pressure of product-storage region 22 may surpass retort pressure 432P such that it breaks the seal allowing some of the air, or other gasses, sealed inside canister 310 to escape between gasket 28 and brim 122 until the pressure of product-storage region 22 is reduced to retort pressure 432P and the seal is reestablished. Once the seal is reestablished, less air or other gasses are stored within product-storage region 22.

As the conveyer moves canister 310 out of oven 48, canister 310 cools to an ambient temperature as suggested in FIG. 21B. Once cooled, product-storage region 22 has a post-retort temperature 434T, pressure 434P, and volume 430V, as suggested below the enlarged perspective view of canister 310 in FIG. 21. Post-retort temperature 434T of product-storage region 22 is similar to pre-retort temperature 430T of product-storage region 22 because the ambient temperature outside of oven 48 is similar before and after oven 48. Post-retort pressure 434P and volume 434V of product-storage region are less than pre-retort pressure 430P and volume 430V of product-storage region 22 due to air or other gasses escaping canister 310 when canister 310 was heated in oven 48.

As canister 10 cools, the pressure of product-storage region 22 is reduced. Elastic barrier film 24 deforms as the pressure of product-storage region 22 reduces to post-retort pressure 434P. Multi-part floating lid 318 assumes the approximately pre-retort shape as elastic barrier film 24 contracts.

Post-retort pressure 434P is less than pre-retort pressure 430P due to air escaping while canister 310 is in oven 48. The ambient pressure outside of canister 310 is higher than post-retort pressure 434P of product-storage region 22 and the ambient pressure applies inward force 52 on elastic barrier film 24 to cause elastic barrier film 24 to deform elastically and depress such that center portion 428 of multi-part floating lid 318 depresses into open mouth 20 as shown in FIGS. 21 and 21. As such, multi-part floating lid 318 assumes the post-retort shape when product-storage region 22 reaches post-retort temperature 434T and pressure 434P. The depression of elastic barrier film 24 reduces the volume of product-storage region 22 such that product-storage region 22 has a post-retort volume 434V that is less than pre-retort volume 430V.

After the seal is first broken during removal of closure 314 from container 12, elastic barrier film 24 contracts and multi-part floating lid 318 resumes the approximately pre-retort shape. As such, the depressed post-retort shape of multi-part floating lid 318 may be an indication that canister 310 has both been through the retort process and the seal between multi-part floating lid 318 and filler neck 88 has not been broken. Such post-retort shape provides a tamper-evident feature to the consumer.

A canister 10 [310] in accordance with the present disclosure comprises a container 12 and a closure 14 [314]. Container 12 is formed to include a product-storage region 22 and includes a body 84 and a filler neck 88 coupled to the body to establish product-storage region 22. Filler neck 88 is formed to include an open mouth 20 that is arranged to open into product-storage region 22.

Closure 14 [314] is adapted to mate with filler neck 88 to close open mouth 20 to block access to product-storage region 22 and establish a variable-volume interior chamber 11 [311] therein. An expansible portion 13 [313] of closure 14 [314] is made of an elastic deformable material and is configured to provide lid means 18 [318] for yielding elastically during exposure of an inner surface 40 [96] of expansible portion 13 [313] of closure 14 [314] to an elevated pressure 132 [432] in excess of a predetermined pressure 130P [430P] that is extant in variable-volume interior chamber 11 [311] when closure 14 [314] is coupled to container 12 and container 12 and the closure 14 [314] are subjected to elevated retort temperatures 132T [434T] to sterilize any product contained in variable-volume interior chamber 11 [311] to cause shape-changing movement of expansible portion 13 [313] of closure 14 [314] from a selected pre-expansion shape in a direction 50 away from container 12 to an outwardly extending inflated shape to cause variable-volume interior chamber 11 [311] to increase in volume and then contracting to assume a contracted shape in response to cooling of variable-volume interior chamber 11 [311].

Lid means 18 [318] includes a lid-reinforcing core 26 [326], an elastic barrier film 24 [123], and a gasket 28. Lid-reinforcing core 26 [326] includes an upwardly facing outer surface 38 [338] arranged to face away from container 12 and a downwardly facing inner surface 40 [340] arranged to face toward container 12. Elastic barrier film 24 [123] is coupled to upwardly facing outer surface 38 [338] of lid-reinforcing core 26 [326]. Gasket 28 is coupled to downwardly facing inner surface 40 [340] of the lid-reinforcing core.

The invention claimed is:

1. A canister comprising
   a container formed to include a product-storage region and including a body and a filler neck coupled to the body to establish the product-storage region and formed to include an open mouth arranged to open into the product-storage region and
   a closure adapted to mate with the filler neck to close the open mouth to block access to the product-storage region and establish a variable-volume interior chamber therein, wherein an expansible portion of the closure is made of an elastic deformable material and is configured to provide lid means, including a monolithic disk comprising plastics materials, for yielding elastically during exposure of an inner surface of the expansible portion of the closure to an elevated pressure in excess of a predetermined pressure that is extant in the variable-volume interior chamber when the closure is coupled to the container and the container and the closure are subjected to elevated retort temperatures to sterilize any product contained in the variable-volume interior chamber to cause shape-changing movement of the expansible portion of the closure from a selected pre-expansion shape in a direction away from the container to an outwardly extending inflated shape to cause the variable-volume interior chamber to increase in volume and then contracting to assume a contracted shape in response to cooling of the variable-volume interior chamber,
   wherein the lid means is configured to break a seal formed between the lid means and the filler neck to allow gases to escape when pressure is increased beyond the elevated pressure and to reestablish the seal when pressure is reduced to at least the elevated pressure,
   wherein the lid means includes a lid-reinforcing core including an upwardly facing outer surface arranged to face away from the container and a downwardly facing inner surface arranged to face toward the container, an elastic barrier film coupled to the upwardly facing outer surface of the lid-reinforcing core, and a gasket coupled to the downwardly facing inner surface of the lid-reinforcing core,
   wherein the lid-reinforcing core is a disk, the disk includes a disk body sized to close the open mouth when the closure is coupled to the filler neck of the container, the disk body having a substantially flat pre-retort shape, and a gasket-receiving track appended to the substantially flat disk body and arranged to extend away from the substantially flat disk body toward the filler neck of the container.

2. The canister of claim 1, wherein the gasket is coupled to the gasket-receiving track and located between the disk body and the filler neck of the container when the closure is coupled to the filler neck.

3. The canister of claim 1, wherein the disk further includes an annular disk-support ring appended to the disk and arranged to extend toward the container, the annular disk-support ring being located between the gasket-receiving track and a closure axis about which the closure is rotated to couple the closure to filler neck.

4. The canister of claim 1, wherein the gasket includes an upper-gasket surface arranged to face toward the lid-reinforcing core, a lower-gasket surface arranged face toward the filler neck of the container, and an outer-gasket edge arranged to extend between and interconnect the upper-gasket surface and the lower-gasket surface and located in spaced-apart radial relation to a closure axis about which the closure is rotated to couple the closure to the filler neck.

5. The canister of claim 4, wherein the gasket further includes an inner-gasket edge arranged to extend between and interconnect the upper-gasket surface and the lower-gasket surface and located between the closure axis and the outer-gasket edge.

6. The canister of claim 1, wherein the elastic barrier film includes a first polymeric layer and a barrier layer coupled to the first polymeric layer and configured to block communication of oxygen through the closure when the closure is coupled to the filler neck of the container.

7. The canister of claim 6, wherein the barrier layer includes one of ethylene vinyl alcohol, a AlOx coated polyethylene terephthalate layer, and a metallic layer.

8. The canister of claim 7, wherein the elastic barrier film further includes a second polymeric layer located in spaced-apart relation to the first polymeric layer to cause the barrier layer to be located between the first polymeric layer and the second polymeric layer.

9. The canister of claim 1, wherein the closure further includes a lid-retainer ring arranged to interconnect the container and the lid means to cause the lid means to be trapped between the lid-retainer ring and the container when the closure is mated the container.

10. The canister of claim 9, wherein the lid-retainer ring includes a top wall arranged to lie in spaced-apart relation above the container when the closure is coupled to the container and an annular side wall appended to the top wall to extend toward the container, the top wall and the annular side wall cooperate to define an interior region therebetween, and the lid means is arranged to lie in the interior region when the closure is coupled to the container and when the closure is spaced apart from and separated from the container.

11. The canister of claim 10, wherein the lid-retainer ring further includes a lid-retainer support appended to the annular side wall and arranged to extend toward the filler neck, the lid-retainer support is spaced apart below the top wall to locate the lid means between the top wall and the lid-retainer support.

12. The canister of claim 11, wherein the lid means is arranged to engage the top wall when the closure is coupled to the filler neck of the container and the lid means is freed to move up and down between the top wall and the lid-retainer support when the closure is spaced apart from the container.

13. The canister of claim 9, wherein the lid-retainer ring is formed to include a lower aperture arranged to open into an interior region formed in the lid-retainer ring and an upper aperture arranged to open into the interior region and the filler neck of the container is arranged to extend into the interior region through the lower aperture when the closure is coupled to the filler neck.

14. The canister of claim 13, wherein the expansible portion of the lid means is located in the interior region of the lid-retainer ring when the closure has the pre-expansion shape.

15. The canister of claim 14, wherein the expansible portion of the lid means is arranged to extend out of the interior region through the upper aperture away from the container when the closure is in the outwardly extending inflated shape.

16. The canister of claim 15, wherein the expansible portion of the lid means is arranged to extend into the product-storage region of the container through the open mouth when the closure is in the contracted shape.

17. The canister of claim 1, wherein the closure further includes a lid-retainer ring arranged to interconnect the container and the lid means to cause the lid means to be trapped between the lid-retainer ring and the container when the closure is mated the container and the lid-retainer ring is formed to include a lower aperture arranged to open into an interior region formed in the lid-retainer ring and an upper aperture arranged to open into the interior region and the filler neck of the container is arranged to extend into the interior region through the lower aperture when the closure is coupled to the filler neck.

18. The canister of claim 17, wherein the expansible portion of the closure is provided by the lid-reinforcing core and the elastic barrier film and portions of the lid-reinforcing core and the elastic barrier film are located in the interior region of the lid-retainer ring when the closure has the selected pre-expansion shape.

19. The canister of claim 17, wherein portions of the lid-reinforcing core and the elastic barrier film are arranged to extend out of the interior region through the upper aperture away from the container when the closure is in the outwardly extending inflated shape.

20. The canister of claim 17, wherein portions of the lid-reinforcing core and the elastic barrier film are arranged to extend into the product-storage region of the container through the open mouth when the closure is in the contracted shape.

21. A canister comprising
a container formed to include a product-storage region and including a body and a filler neck coupled to the body to establish the product-storage region and formed to include an open mouth arranged to open into the product-storage region and
a closure adapted to mate with the filler neck to close the open mouth to block access to the product-storage region and establish a variable-volume interior chamber therein, wherein an expansible portion of the closure is made of an elastic deformable material which yields elastically during exposure of an inner surface of the expansible portion of the closure to an elevated pressure in excess of a predetermined pressure that is extant in the variable-volume interior chamber when the closure is coupled to the container and the container and the closure are subjected to elevated retort temperatures to cause shape-changing movement of the expansible portion of the closure from a selected pre-expansion shape in a direction away from the container to an outwardly extending inflated shape to cause the variable-volume interior chamber to increase in volume and then contracting to assume a contracted shape in response to cooling of the variable-volume interior chamber, wherein the closure includes a lid including a monolithic plastics materials disk and an elastic barrier film arranged to close the open mouth of the container and a lid-retainer ring arranged to interconnect the container and the lid when the closure is coupled to the container and wherein the lid is configured to break a seal formed between the lid and the filler neck to allow gases to escape when pressure is increased beyond the elevated pressure and to reestablish the seal when pressure is reduced to at least the elevated pressure, wherein the disk includes a disk body sized to close the open mouth when the closure is coupled to the filler neck of the container, the disk body having a substantially flat pre-retort shape, and a gasket-receiving track appended to the substantially flat disk body and arranged to extend toward the filler neck of the container, wherein a gasket is arranged in the gasket-receiving track.

22. The canister of claim 18, wherein the lid is trapped between the lid-retainer ring and the container when the closure is mated the container and the lid-retainer ring is formed to include a lower aperture arranged to open into an interior region formed in the lid-retainer ring and an upper aperture arranged to open into the interior region and the filler neck of the container is arranged to extend into the interior region through the lower aperture when the closure is coupled to the filler neck.

23. The canister of claim 22, wherein the expansible portion of the closure located in the interior region of the lid-retainer ring when the closure has the selected pre-expansion shape.

24. The canister of claim 23, wherein the expansible portion of the closure is arranged to extend out of the interior region through the upper aperture away from the container when the closure is in the outwardly extending inflated shape.

25. The canister of claim 18, wherein the expansible portion of the closure is arranged to extend into the product-storage region of the container through the open mouth when the closure is in the contracted shape.

26. The canister of claim 25, wherein the expansible portion of the closure is provided by the lid-reinforcing core and the elastic barrier film.

27. A closure comprising
a floating lid and
a lid-retainer ring adapted to interconnect the floating lid and a filler neck of a container to cause the floating lid to be fixed in position relative to the filler neck, wherein the floating lid includes a lid-reinforcing plastics material core including an upwardly facing outer surface arranged to face in an upward direction and a downwardly facing inner surface arranged to face in an opposite downward direction, an elastic barrier film coupled to the upwardly facing outer surface of the lid-reinforcing core, and a gasket coupled to the downwardly facing inner surface of the lid-reinforcing core, wherein the floating lid includes an expansible portion made of an elastic deformable material which yields elastically during exposure of an inner surface of the expansible portion of the floating lid to retort sterilization temperatures and an elevated pressure in excess of a predetermined pressure that is extant when the floating lid is fixed in position relative to the filler neck, to cause shape-changing movement of the expansible portion from a selected pre-expansion shape in the upward direction to an outwardly extending inflated shape and then contracting in the downward direction to assume a contracted shape in response to removal of the elevated pressure; wherein the floating lid is configured to break a seal formed between the floating lid and the filler neck to allow gases to escape when pressure is increased beyond the elevated pressure and to reestablish the seal when pressure is reduced to at least the elevated pressure, wherein the expansible portion comprises a disk including a disk body sized to close an open mouth of the filler neck when the closure is coupled to the filler neck of the container, the disk body having a substantially flat pre-retort shape, and a gasket-receiving track appended to the substantially flat disk body and arranged to receive the gasket and to extend toward the filler neck of the container.

28. The canister of claim 27, wherein the expansible portion of the closure is located in an interior region formed in the lid-retainer ring when the closure is in the selected pre-expansion shape.

29. The canister of claim 28, wherein the expansible portion of the closure is arranged to extend out of the interior region through an upper aperture formed in the lid-retainer ring when the closure is in the outwardly extending inflated shape.

30. The canister of claim 29, wherein the expansible portion of the closure is provided by the lid-reinforcing core and the elastic barrier film.

* * * * *